United States Patent
Herweijer et al.

(12) 
(10) Patent No.: US 7,192,605 B2
(45) Date of Patent: *Mar. 20, 2007

(54) NUCLEIC ACID TRANSFER COMPLEXES

(75) Inventors: Hans Herweijer, Madison, WI (US); Vladimir G. Budker, Middleton, WI (US)

(73) Assignee: Mirus Bio Corporation, Madison, WI (US)

( * ) Notice: Subject to any disclaimer, the term of this patent is extended or adjusted under 35 U.S.C. 154(b) by 382 days.

This patent is subject to a terminal disclaimer.

(21) Appl. No.: 10/161,241

(22) Filed: May 31, 2002

(65) Prior Publication Data

US 2003/0044983 A1    Mar. 6, 2003

Related U.S. Application Data (62) Division of application No. 09/709,656, filed on Nov. 10, 2000, now Pat. No. 6,458,382.

(60) Provisional application No. 60/165,211, filed on Nov. 12, 1999.

(51) Int. Cl.
 *A61K 9/127* (2006.01)
 *A61K 31/7088* (2006.01)
 *C12N 15/88* (2006.01)

(52) U.S. Cl. ............... 424/450; 435/455; 435/458; 514/44

(58) Field of Classification Search ........... 435/458, 435/455
See application file for complete search history.

(56) References Cited

U.S. PATENT DOCUMENTS

| | | | |
|---|---|---|---|
| 5,552,157 A * | 9/1996 | Yagi et al. ............... 424/450 |
| 5,976,567 A * | 11/1999 | Wheeler et al. ........... 424/450 |
| 6,228,391 B1 * | 5/2001 | Shimizu et al. ........... 424/450 |
| 6,235,310 B1 * | 5/2001 | Wang et al. ............... 424/450 |
| 6,458,382 B1 * | 10/2002 | Herweijer et al. ......... 424/450 |

FOREIGN PATENT DOCUMENTS

| | | | |
|---|---|---|---|
| WO | WO97/42166 | * 11/1997 | ................. 424/450 |

* cited by examiner

*Primary Examiner*—Scott D. Priebe
*Assistant Examiner*—Michael Burkhart
(74) *Attorney, Agent, or Firm*—Mark K. Johnson; Kirk Ekena

(57) ABSTRACT

The present invention relates to compositions and methods for transferring nucleic acids into cells in vitro and in vivo. The compositions comprise a transfection reagent and one or more detergents. In preferred embodiments, the compositions comprise delivery systems providing nucleic acid transfer complexes that transfect cells with high efficiency.

7 Claims, 4 Drawing Sheets

NUCLEIC ACID TRANSFER COMPLEXES

CROSS-REFERENCE TO RELATED APPLICATIONS

This application is a divisional of U.S. application Ser. No. 09/709,656, filed Nov. 10, 2000, now U.S. Pat. No. 6,458,382 which claims benefit of U.S. Provisional Application 60/165,211, filed Nov. 12, 1999.

FIELD OF THE INVENTION

The present invention relates to compositions and methods for transferring nucleic acids into cells in vitro and in viva. The compositions comprise a transfection reagent and one or more detergents. In preferred embodiments, the compositions comprise delivery systems providing nucleic acid transfer complexes that transfect cells with high efficiency.

BACKGROUND OF TILE INVENTION

The efficient delivery of biologically active compounds to the intracellular space of cells has been accomplished by the use of a wide variety of vesicles. One particular type of vesicle, liposomes, is one of the most developed types of vesicles for drug delivery. Liposomes are microscopic vesicles that comprise amphipathic molecules that contain both hydrophobic and hydrophilic regions. Liposomes can contain an aqueous volume that is entirely enclosed by a membrane composed of amphipathic molecules (usually phospholipids).

Liposome drug carriers have been under development since the 1970's. Liposomes are formed from one to several different types of amphipathic molecules. Several methods have also been developed to complex biologically active compounds wit liposomes. For example, a biologically active compound can be entrapped within the internal aqueous phase, within the lipid phase, or complexed to the outside of the liposome.

Liposomes can be divided into three groups based upon their overall size and lamellar structure. Small uni-lamellar vesicles (SUV), which are typically prepared by sonication, are 20 to 30 nm in diameter and contain one single lipid bilayer surrounding the aqueous compartment. Multi-lamellar vesicles (MLV) are prepared by simply mixing amphipathic molecules in an aqueous phase and contain multiple aqueous compartments and bilayers. Large uni-lamellar vesicles (LUV) are most commonly prepared by reverse-phase evaporation. After subsequent pore filtration, LUV's are usually 150 to 200 nm in diameter.

Liposomes can also be classified according to mechanisms by which they attach to a target cell. Gangliosides, polysacharrides and polymers such as polyethylene glycol have been attached to liposomes (termed "Stealth Liposomes") to decrease their non-specific uptake by the reticuloendothelial system in vivo. Antibodies, polysaccharides, sugars, and other ligands have been attached to liposomes to enable the tissue and cell specific delivery of biologically active compounds. Other cellular and viral proteins have also been incorporated into liposomes for targeting purposes and for their fusogenic properties.

Liposomes typically deliver a biologically active compound found within their aqueous space to target cells by fusing with either the plasma membrane or an internal membrane of the cell after endocytosis of the liposome. Fusion of the liposome membrane with the cellular membrane is one of the critical steps in the efficient delivery of substances to the cell. Certain types of liposomes are endocytosed by certain types of cells. If a liposome is endocytosed by a receptor-mediated pathway, then it enters an endosome. In order for the biologically active compound contained within or associated with the liposome to reach its target sites and receptors, it is essential that the compound escape or be released from the endosome and avoid degradation in the lysosomes.

Efficient nucleic acid transfer in vitro has been accomplished with the use of positively-charged liposomes that contain cationic lipids. For example, the cationic lipid, N-1-(2,3dioleyloxy)propyl-N,N,N-trimethylammonium chloride (DOTMA) was the first cationic lipid used for DNA transfections. DOTMA was combined with dioleoylphosphatidylethanolamine (DOPE) to form liposomes that spontaneously complexed with nucleic acids (DNA and RNA) and provided relatively efficient transfections. Other neutral lipids have been used in conjunction with amphipathic compounds to form liposomes. These have generally been chosen from the group consisting of phosphatidylethanolamines (e.g., DOPE), phosphatidylcholines, or phosphatidylserines, wherein the acyl group chain length is between 16 and 20. Another compound used to form liposomes suitable for transfecting nucleic acids into cells is cholesterol.

These liposomes are simply mixed with the nucleic acid and then applied to the cells in culture. Complete entrapment of the DNA or RNA molecules occurs because the positively-charged liposomes naturally complex with negatively-charged nucleic acids. DNA has been shown to induce fusion of cationic liposomes containing DOTMA/DOPE. The procedure with the cationic lipids is generally as or more efficient than the commonly-used procedure involving the co-precipitation of calcium phosphate and DNA.

DOTMA/DOPE liposomes have, however, substantial cytotoxicity, particularly in vivo. A variety of cationic lipids have been made in which a glycerol or cholesterol hydrophobic moiety is linked to a cationic headgroup by metabolically degradable ester bond. These have included 1,2-bis(oleoyloxy)-3-(4'-trimethylammonio)propane (DOTAP), 1,2-dioleoyl-3-(4'-trimethylammonio)butanoyl-sn-glycerol (DOTB), 1,2-dioleoyl-3-succinyl-sn-glycerol choline ester (DOSC) and cholesteryl (4'-trimethylammonio)butanoate (ChoTB). However, there is no evidence of reduced cytotoxicity in comparison of these ester bond-containing cationic lipids as compared to DOTMA. Stearylamine, a cationic lipid has been used in liposomes but it had great cytotoxicity and was not been reported to mediate DNA transfer. Another detergent, cetyltrimethylammonium bromide (CTAB), when combined with DOPE, was able to mediate DNA transfection, but it had significant cytotoxicity. A series of cationic, non-pH sensitive lipids that included DORI (1,2-dioleoyl-3-dimethyl-hydroxyethyl ammonium bromide), DORIE (1,2-dioleyloxypropyl-3-dimethyl-hydroxyethyl ammonium bromide), and DMRIE (1,2-dimyristyloxypropyl-3-dimethyl-hydroxyethyl ammonium bromide) have been reported and studied. Other non-pH-sensitive, cationic lipids include: O,O'-didodecyl-N-p-(2-trimethylammonioethyloxy)benzoyl-N,N,N-trimethylammonium chloride, Lipospermine, DC-Chol (3á-N-(N',N"-dimethylaminoethane)carbonylcholesterol), lipopoly(L-lysine), cationic multilamellar liposomes containing N-(à-trimethylammonioacetyl)-didodecyl-D-glutamate chloride (TMAG), TRANSFECTACE (1:2.5 (w:w) ratio of DDAB which is dimethyl dioctadecylammonium bromide and DOPE) (Life Technologies) and LIPO- FECTAMINE (3:1 (w:w) ratio of DOSPA which is 2,3-dioleyloxy-N-20({2,5-bis (3-aminopropyl)amino-1-oxypentyl}amino)ethyl-N,N-dimethyl-2,3-bis(9-octadecenyloxy)-1-propanaminium trifluoroacetate and DOPE) (Life Technologies). While much development has occurred, the art is still in need of improved transfection compositions and methods for providing efficient, low toxicity delivery of agents in vitro and in vivo.

Furthermore, most transfection reagents have been optimized to transfect mammalian cells. In vitro, these cells are generally maintained at 37° C. Only two commercially available transfection reagents are claimed to be most efficient for the transfection of insect cells, which are maintained at a temperature of 25–27° C. Studies on cell membrane composition demonstrated that there are significant composition differences between mammalian and insect cells. Thus, the art is also in need of efficient, low toxicity delivery systems for the delivery of agents to cells other than mammalian cells or to cells under non-standard growth conditions.

SUMMARY OF THE INVENTION

The present invention relates to compositions and methods for transferring nucleic acids into cells in vitro and in vivo. The compositions comprise a transfection reagent and one or more detergents. In preferred embodiments, the compositions comprise one or more amphipathic compounds and one or more neutral lipids. In preferred embodiments, the compositions comprise delivery systems providing nucleic acid transfer complexes that transfect cells with high efficiency. The transfection complexes of the present invention find use, for example, in the high-efficiency transfection of cells. A variety of cells may be transfected with high efficiency using the compositions and methods of the present invention, including, but not limited to, insect cells and keratinocytes. As demonstrated by the data herein, the transfection complexes of the present invention provides substantially higher transfection efficiencies than available systems.

In some embodiments of the present invention, the transfection complex comprises an amphipathic compound, a neutral lipid, and a detergent. In some preferred embodiments, the detergent comprises a short lipid chain (e.g., dilauroyl phosphatidylethanolamine [DLPE]). Such complexes significantly alter the efficiency for transferring nucleic acids into cell types that are maintained in non-traditional conditions (i.e., non-mammalian cell types maintained, for example, at temperature other than 37° C.), as well as cells that are maintained under standard or traditional conditions. For example, in some preferred embodiments, the transfection complex comprises the amphipathic compound DOTAP, which is mixed with the neutral lipid DOPE, and the detergent DLPE. Although any suitable combination of the components may be used (e.g., any combination that permits transfection of cells), in particularly preferred embodiments, the components are provided in a ratio of 10:9:1 (DOTAP:DOPE:DLPE, w:w:w), respectively.

In some embodiments of the present invention, the transfection complex comprises an amphipatic compound and a nucleic acid-binding protein. Preferably, the DNA-binding protein is cationic (net positive charge) such as a histone protein. H1 histone protein is the preferred histone type. In yet another preferred embodiment, histone H1 protein is used as a DNA-binding protein and 1,4-bis(3-oleoylamido propyl)piperazine is used for the amphipathic compound. In preferred embodiments, a detergent is added to the transfection reagent mixture (e.g., DLPE or CHAPS).

In some embodiments of the present invention, the transfection complex comprises an amphipathic compound, a cationic protein, and a neutral lipid. Such complexes significantly alter the efficiency for transferring nucleic acids into certain cell types. For example, in some preferred embodiments, the transfection complex comprises the amphipathic compound 1,4-bis(3-oleoylamidopropyl) piperazine, the protein histone H1, and the neutral lipid DLPE. In particularly preferred embodiments, the components are provided in a ratio of 1:3:0.125 (w:w:w).

In some embodiments of the present invention, the transfection complex comprises an amphipathic compound, a cationic protein, and a detergent. In some preferred embodiments, the detergent comprises 3-[(cholamidopropyl)dimethylammonio]-1-propanesulfonate (CHAPS). Such complexes significantly alter the efficiency for transferring nucleic acids into certain cell types. For example, in some preferred embodiments, the transfection complex comprises the amphipathic compound 1,4-bis(3-oleoylamidopropyl) piperazine, the protein histone H1, and the detergent CHAPS. In particularly preferred embodiments, the components are provided in a ratio of 1:3:0.25 (w:w:w).

In some embodiments, the present invention provides a process of delivering a biologically active substance to a cell comprising exposing the cell to the biologically active substance in the presence of a delivery system of the present invention. In a preferred embodiment, the biologically active substance is a nucleic acid. In preferred embodiments, the delivery system comprises liposomes that are complexed with the nucleic acid.

In preferred embodiments, the present invention provides a process for delivering nucleic acids into insect cells. While the present invention is not limited by the nature of the insect cells, in preferred embodiments the insect cells are Sf9, Sf21, High Five, or S2 cells.

In preferred embodiments, the present invention provides a process for delivering nucleic acids into keratinocytes. While the present invention is not limited by the nature of the keratinocytes, in preferred embodiments the keratinocytes are NIKS (Normal Immortalized Keratinocyte that produce Skin).

In preferred embodiments, the present invention provides a process for delivering nucleic acids into 293 cells.

The present invention further provides compositions comprising a transfection complex (e.g., liposome), wherein the transfection complex comprises a detergent. For example, in some embodiments, the transfection complex comprises amphipathic compounds. In other preferred embodiments, the transfection complex is capable of complexing nucleic acids. In preferred embodiments, the detergent comprises lipids (e.g., phospholipids) with acyl chains shorter than 18 carbons, more preferably shorter than 16 carbons or less (e.g., 15, 14, 13, 12, . . . ). In yet other preferred embodiments, the detergent has a critical micelle concentration equal to or higher than dipalmitoylphosphatidylcholine (DPPC).

The present invention also provides a composition for transfecting cells comprising an amphipatic compound; a lipid, said lipid comprising phospholipid, glycolipid, sphingosin-containing lipid, cholesterol or combinations thereof, said phospholipid, glycolipid, and sphingosin-containing lipid comprising an acyl group chain length equal to or longer than 16 carbons; and a detergent. While the present invention is not limited to any particular ratio of the consitituents, in preferred embodiments, the molar ratio of the amphipathic compound to the lipids is from 10:1 to 1:10. In preferred embodiments, the detergent comprises a neutral lipid with an acyl chain length equal to or smaller than 16 carbons. While the present invention is not limited to any particular ratio of the consitituents, in preferred embodiments, the molar ratio of the lipid to the detergent is from 100:1 to 1:100. Suitable detergents for use with the present invention include, but are not limited to, dilauroylphosphatidylethanolamine (DLPE), dilauroylphosphatidylcholine (DLPC), and 3-[(cholamidopropyl)dimethylammonio]-1-propanesulfonate (CHAPS).

In some preferred embodiments, the present invention further provides a composition comprising 1,2-bis(oleoyloxy)-3-(4'-trimethylammonio)propane (DOTAP), dioleoylphosphatidylethanolamine (DOPE), and DLPE. While the present invention is not limited to any particular ratio of the consitituents, in preferred embodiments, the molar ratio of DOTAP to phospolipids is approximately 1:1 and wherein the ratio of DOPE to DLPE is 100:1 to 1:100. For example, is some embodiments, the ratio of DOPE to DLPE is approximately 19:1 or 9:1.

The present invention also provides a composition comprising DOTAP, DOPE, and DLPC wherein the ratio of DOTAP to neutral lipids is approximately 1:1 and wherein the ratio of DOPE to DLPC is 100:1 to 1:100. For example, in some embodiments, the ratio of DOPE to DLPC is approximately 19:1 or 9:1.

The present invention further provides a composition comprising: amphipathic compounds capable of complexing nucleic acids; cationic polymers; and a lipid selected from the group consisting of phospholipids, glycolipids, cholesterol, and sphingosin-containing lipids, wherein the acyl group chain length of said lipid is smaller than 16 carbons; wherein the molar ratio of the amphipathic compounds to the lipids is 100:1 to 1:100. In preferred embodiments, the lipid is dilauroylphosphatidylethanolamine (DLPE) or 3-[(cholamidopropyl)dimethylammonio]-1-propanesulfonate (CHAPS).

The present invention also provides a composition comprising 1,4-bis(3-oleoylamidopropyl) piperazine, histone H1, and detergent. In some preferred embodiments, the ratio of 1,4-bis(3-oleoylamidopropyl) piperazine to histone H1 is 3 to 1, and the ratio of 1,4-bis(3-oleoylamidopropyl) piperazine to detergent is 100:1 to 1:100. In some preferred embodiments, the detergent is DLPE or CHAPS. In particularly preferred embodiments, the ratio of 1,4-bis(3-oleoylamidopropyl) piperazine to histone H1 to detergent is 3:1: 0.125.

The present invention further provides kits containing any of the transfection complexes described herein. Such kits may further comprise cells for transfection, instructions, and control materials. In some preferred embodiments, the kits comprise a transfection complex, said transfection complex comprising a detergent. For example, in some embodiments, the detergent comprises phospholipids with acyl chains shorter than 16 carbons.

DETAILED DESCRIPTION OF THE INVENTION

I. Definitions

To facilitate an understanding of the present invention, a number of terms and phrases are defined below:

The term "nucleic acid" is a term of art that refers to a polymer containing at least two nucleotides. "Nucleotides" contain a sugar deoxyribose (DNA) or ribose (RNA), a base, and a phosphate group. Nucleotides are the monomeric units of nucleic acid polymers. Nucleotides are linked together through the phosphate groups to form nucleic acid. A "polynucleotide" is distinguished here from an "oligonucleotide" by containing more than 100 monomeric units; oligonucleotides contain from 2 to 100 nucleotides. "Bases" include purines and pyrimidines, which further include natural compounds adenine, thymine, guanine, cytosine, uracil, inosine, and other natural analogs, and synthetic derivatives of purines and pyrimidines, which include, but are not limited to, modifications which place new reactive groups such as, but not limited to, amines, alcohols, thiols, carboxylates, and alkylhalides. The term nucleic acid includes deoxyribonucleic acid ("DNA") and ribonucleic acid ("RNA"). The term nucleic acid encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

Nucleic acids may be linear, circular, or have higher orders of topology (e.g., supercoiled plasmid DNA). DNA may be in the form of anti-sense, plasmid DNA, parts of a plasmid DNA, vectors (P1, PAC, BAC, YAC, artificial chromosomes), expression cassettes, chimeric sequences, chromosomal DNA, or derivatives of these groups. RNA may be in the form of oligonucleotide RNA, tRNA (transfer RNA), snRNA (small nuclear RNA), rRNA (ribosomal RNA), mRNA (messenger RNA), anti-sense RNA, (interfering) double stranded RNA, ribozymes, chimeric sequences, or derivatives of these groups. "Anti-sense" is a nucleic acid that interferes with the function of DNA and/or RNA. This may result in suppression of expression. Interfering RNA ("RNAi") is double stranded RNA that results in catalytic degradation of specific mRNAs, and can also be used to lower gene expression. Natural nucleic acids have a phosphate backbone; artificial nucleic acids may contain other types of backbones, nucleotides, or bases. Artificial nucleic acids with modified backbones include peptide nucleic acids (PNAs), phosphothionates, phosphorothioates, phosphorodiamidate morpholino, and other variants of the phosphate backbone of native nucleic acids.

Examples of modified nucleotides include methylation, mustard addition, and aromatic nitrogen mustard addition. "Mustards" include nitrogen mustards and sulfur mustards. Mustards are molecules consisting of a nucleophile and a leaving group separated by an ethylene bridge. After internal attack of the nucleophile on the carbon bearing the leaving group a strained three membered group is formed. This strained ring (in the case of nitrogen mustards an aziridine ring is formed) is very susceptible to nucleophilic attack. Thus allowing mustards to alkylate weak nucleophiles such as nucleic acids. Mustards can have one of the ethylene bridged leaving groups attached to the nucleophile, these molecules are sometimes referred to as half-mustards; or they can have two of the ethylene bridged leaving groups attached to the nucleophile, these molecules can be referred to as bis-mustards. A "nitrogen mustard" is a molecule that contains a nitrogen atom and a leaving group separated by an ethylene bridge, i.e. $R_2NCH_2CH_2X$ where R=any chemical group, and X=a leaving group typically a halogen. An "aromatic nitrogen mustard" is represented by $RR'NCH_2CH_2X$ (wherein R=any chemical group, N=nitrogen, X=a leaving group, typically a halogen, R'=an aromatic ring, R=any chemical group).

Nucleic acid may be single ("ssDNA"), double ("dsDNA"), triple ("tsDNA"), or quadruple ("gsDNA") stranded DNA, and single stranded RNA ("RNA") or double stranded RNA ("dsRNA"). "Multistranded" nucleic acid contains two or more strands and can be either homogeneous as in double stranded DNA, or heterogeneous, as in DNA/RNA hybrids. Multistranded nucleic acid can be full length multistranded, or partially multistranded. It may further contain several regions with different numbers of nucleic acid strands. Partially single stranded DNA is considered a sub-group of ssDNA and contains one or more single stranded regions as well as one or more multiple stranded regions.

"Preparation of single stranded nucleic acid": Single stranded nucleic acids can be generated by a variety of means, including denaturation, separation, chemical synthesis, isolation from viruses, enzymatic reaction. "Denaturation" is the process in which multi-stranded nucleic acid is completely or partially separated into single stranded nucleic acids. This can proceed through heating, alkaline treatment, or the addition of chemicals such as chaotropic salts or organic solvents (e.g., formamide). A mixture of nucleic acids can be "separated" by physical means such as density gradient centrifugation, gel electrophoresis, or affinity purification. Affinity purification can be accomplished by incorporating a ligand in the nucleic acid (e.g., biotin), and using the corresponding ligate (e.g., strepavidin) bound to a matrix (e.g., magnetic beads) to specifically bind and purify this nucleic acid. "Chemical synthesis" refers to the process where a single stranded nucleic acid is formed by repetitively attaching a nucleotide to the end of an existing nucleic acid. The existing nucleic acid can be a single nucleotide. Single stranded oligonucleotides can be chemically linked together to form long nucleic acids. "Viral" nucleic acids are isolated from viruses. These viruses can infect prokaryotes (e.g., M13, T7, lambda) or eukaryotes (e.g., adeno-associated virus [AAV], adenovirus, retrovirus, herpesvirus, Sindbis virus). Isolation from single stranded DNA viruses (Families of Hepadnaviridae, Circoviridae, Parvoviridae, Inoviridae, Microviridae, and Geminiviridae) will directly generate (partially) single stranded DNA.

"Enzymatic reaction" refers to processes mediated by enzymes. One strand of a double stranded nucleic acid can be preferentially degraded into nucleotides using a nuclease. Many ribonucleases are known with specific activity profiles that can be used for such a process. For instance, RNase H can be used to specifically degrade the RNA strand of an RNA-DNA double stranded hybrid nucleic acid, which in itself may have been formed by the enzymatic reaction of reverse transcriptase synthesizing the DNA stranded using the RNA strand as the template. Following the introduction of a nick, a ribonuclease can specifically degrade the strand with the nick, generating a partially single stranded nucleic acid. A RNA or DNA dependent DNA polymerase can synthesize new DNA which can subsequently be isolated (e.g., by denaturation followed by separation). The polymerase chain reaction process can be used to generate nucleic acids. Formation of single stranded nucleic acid can be favored by adding one oligonucleotide primer in excess over the other primer ("asymmetric PCR"). Alternatively, one of the DNA strands formed in the PCR process may be separated from the other (e.g., by using a ligand in one of the primers).

"Expression cassette" refers to a natural or recombinantly produced nucleic acid molecule that is capable of expressing protein(s). A DNA expression cassette typically includes a promoter (allowing transcription initiation), and a sequence encoding one or more proteins. Optionally, the expression cassette may include trancriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include translation termination signals, a polyadenosine sequence, internal ribosome entry sites (IRES), and non-coding sequences. A nucleic acid can be used to modify the genomic or extrachromosomal DNA sequences. This can be achieved by delivering a nucleic acid that is expressed. Alternatively, the nucleic acid can effect a change in the DNA or RNA sequence of the target cell. This can be achieved by hybridization, multistrand nucleic acid formation, homologous recombination, gene conversion, or other yet to be described mechanisms.

The term "gene" generally refers to a nucleic acid sequence that comprises coding sequences necessary for the production of a therapeutic nucleic acid (e.g., ribozyme) or a polypeptide or precursor. The polypeptide can be encoded by a full length coding sequence or by any portion of the coding sequence so long as the desired activity or functional properties (e.g., enzymatic activity, ligand binding, signal transduction) of the full-length polypeptide or fragment are retained. The term also encompasses the coding region of a gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as "5' untranslated sequences." The sequences that are located 3' or downstream of the coding region and which are present on the mRNA are referred to as "3' untranslated sequences." The term gene encompasses both cDNA and genomic forms of a gene. A genomic form or clone of a gene contains the coding region interrupted with "non-coding sequences" termed "introns" or "intervening regions" or "intervening sequences." Introns are segments of a gene which are transcribed into nuclear RNA. Introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. The term non-coding sequences also refers to other regions of a genomic form of a gene including, but not limited to, promoters, enhancers, transcription factor binding sites, polyadenylation signals, internal ribosome entry sites, silencers, insulating sequences, matrix attachment regions. These sequences may be present close to the coding region of the gene (within 10,000 nucleotide) or at distant sites (more than 10,000 nucleotides). These non-coding sequences influence the level or rate of transcription and translation of the gene. Covalent modification of a gene may influence the rate of transcription (e.g., methylation of genomic DNA), the stability of mRNA (e.g., length of the 3' polyadenosine tail), rate of translation (e.g., 5' cap), nucleic acid repair, and immunogenicity. One example of covalent modification of nucleic acid involves the action of LabelIT reagents (Mirus Corporation, Madison, Wis.).

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence. As used herein, the terms "an oligonucleotide having a nucleotide sequence encoding a gene," "a polynucleotide having a nucleotide sequence encoding a gene," and "a nucleic acid having a nucleotide sequence encoding a gene," mean a nucleic acid sequence comprising the coding region of a gene or in other words the nucleic acid sequence which encodes a gene product. The coding region may be present in either a cDNA, genomic DNA or RNA form. When present in a DNA form, the nucleic acid may be single-stranded, double-stranded, multistranded, partially single stranded, or partially multistranded. Suitable control elements such as, but not limited to, enhancers/promoters, splice junctions, and polyadenylation signals, may be placed in close proximity to the coding region of the gene if needed to permit proper initiation of transcription and correct processing of the primary RNA transcript. Alternatively, the coding region utilized in the expression vectors may contain endogenous enhancers/promoters, splice junctions, intervening sequences, polyadenylation signals; exogenous control elements; or a combination of both endogenous and exogenous control elements.

The term "isolated" when used in relation to a nucleic acid, as in "an isolated nucleic acid" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, "non-isolated nucleic acids" are nucleic acids, such as DNA and RNA, found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid may be present in single stranded, partially single stranded, multistranded, or partially multistranded form.

As used herein, the term "gene expression" refers to the process of converting genetic information encoded in a gene into RNA (e.g., mRNA, rRNA, tRNA, or snRNA) through "transcription" of a deoxyribonucleic gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

Two molecules are combined, to form a "complex" through a process called "complexation" or "complex formation," if the are in contact with one another through "non-covalent" interactions such as, but not limited to, electrostatic interactions, hydrogen bonding interactions, and hydrophobic interactions. An "interpolyelectrolyte complex" is a non-covalent interaction between polyelectrolytes of opposite charge. A molecule is "modified," through a process called "modification," by a second molecule if the two become bonded through a covalent bond. That is, the two molecules form a covalent bond between an atom form one molecule and an atom from the second molecule resulting in the formation of a new single molecule. A chemical "covalent bond" is an interaction, bond, between two atoms in which there is a sharing of electron density.

The terms "naked nucleic acid" and "naked polynucleotide" indicate that the nucleic acid or polynucleotide is not associated with a transfection reagent or other delivery vehicle that is required for the nucleic acid or polynucleotide to be delivered to the cell. A "transfection reagent" is a compound or compounds that bind(s) to or complex(es) with oligonucleotides and polynucleotides, and mediates their entry into cells. The transfection reagent also mediates the binding and internalization of oligonucleotides and polynucleotides into cells. Examples of transfection reagents include cationic liposomes and lipids, polyamines, calcium phosphate precipitates, histone proteins, polyethylenimine, and polylysine complexes. It has been shown that cationic proteins like histones and protamines, or synthetic polymers like polylysine, polyarginine, polyornithine, DEAE dextran, polybrene, and polyethylenimine may be effective intracellular delivery agents, while small polycations like spermine are ineffective. Typically, the transfection reagent has a net positive charge that binds to the oligonucleotide's or polynucleotide's negative charge. The transfection reagent mediates binding of oligonucleotides and polynucleotides to cells via its positive charge (that binds to the cell membrane's negative charge) or via ligands that bind to receptors in the cell. For example, cationic liposomes or polylysine complexes have net positive charges that enable them to bind to DNA or RNA. Polyethylenimine, which facilitates gene transfer without additional treatments, probably disrupts endosomal function itself.

Other vehicles are also used, in the prior art, to transfer genes into cells. These include complexing the nucleic acids on particles that are then accelerated into the cell. This is termed "biolistic" or "gun" techniques. Other methods include electroporation, microinjection, liposome fusion, protoplast fusion, viral infection, and iontophoresis.

"Intravascular" refers to an intravascular route of administration that enables a polymer, oligonucleotide, or polynucleotide to be delivered to cells more evenly distributed and more efficiently than direct injections. Intravascular herein means within an internal tubular structure called a vessel that is connected to a tissue or organ within the body of an animal, including mammals. Within the cavity of the tubular structure, a bodily fluid flows to or from the body part. Examples of bodily fluid include blood, lymphatic fluid, or bile. Examples of vessels include arteries, arterioles, capillaries, venules, sinusoids, veins, lymphatics, and bile ducts. The intravascular route includes delivery through the blood vessels such as an artery or a vein. "Intracoronary" refers to an intravascular route for delivery to the heart wherein the blood vessels are the coronary arteries and veins.

Delivery of a nucleic acid means to transfer a nucleic acid from a container outside a mammal to near or within the outer cell membrane of a cell in the mammal. The term "transfection" is used herein, in general, as a substitute for the term "delivery," or, more specifically, the transfer of a nucleic acid from directly outside a cell membrane to within the cell membrane. If the nucleic acid is a primary RNA transcript that is processed into messenger RNA, a ribosome translates the messenger RNA to produce a protein within the cytoplasm. If the nucleic acid is a DNA, it enters the nucleus where it is transcribed into a messenger RNA that is transported into the cytoplasm where it is translated into a protein. Therefore if a nucleic acid expresses its cognate protein, then it must have entered a cell. A protein may subsequently be degraded into peptides, which may be presented to the immune system.

A "therapeutic gene" refers herein to a nucleic acid that may have a therapeutic effect upon transfection into a cell. This effect can be mediated by the nucleic acid itself (e.g., anti-sense nucleic acid), following transcription (e.g., anti-sense RNA, ribozymes, interfering dsRNA), or following expression into a protein. "Protein" refers herein to a linear series of greater than 2 amino acid residues connected one to another as in a polypeptide. A "therapeutic" effect of the protein in attenuating or preventing the disease state can be accomplished by the protein either staying within the cell, remaining attached to the cell in the membrane, or being secreted and dissociated from the cell where it can enter the general circulation and blood. Secreted proteins that can be therapeutic include hormones, cytokines, growth factors, clotting factors, anti-protease proteins (e.g., alpha1-antitrypsin), angiogenic proteins (e.g., vascular endothelial growth factor, fibroblast growth factors), antiangiogenic proteins (e.g., endostatin, angiostatin), and other proteins that are present in the blood. Proteins on the membrane can have a therapeutic effect by providing a receptor for the cell to take up a protein or lipoprotein. Therapeutic proteins that stay within the cell (intracellular proteins) can be enzymes that clear a circulating toxic metabolite as in phenylketonuria. They can also cause a cancer cell to be less proliferative or cancerous (e.g., less metastatic), or interfere with the replication of a virus. Intracellular proteins can be part of the cytoskeleton (e.g., actin, dystrophin, myosins, sarcoglycans, dystroglycans) and thus have a therapeutic effect in cardiomyopathies and musculoskeletal diseases (e.g., Duchenne muscular dystrophy, limb-girdle disease). Other therapeutic proteins of particular interest to treating heart disease include polypeptides affecting cardiac contractility (e.g., calcium and sodium channels), inhibitors of restenosis (e.g., nitric oxide synthetase), angiogenic factors, and anti-angiogenic factors.

"Vectors" are nucleic acid molecules originating from a virus, a plasmid, or the cell of an organism into which another nucleic fragment of appropriate size can be integrated without loss of the vectors capacity for self-replication. Vectors introduce nucleic acids into host cells, where it can be reproduced. Examples are plasmids, cosmids, and yeast artificial chromosomes. Vectors are often recombinant molecules containing nucleic acid sequences from several sources. Vectors include viruses, for example adenovirus (an icosahedral (20-sided) virus that contains DNA; there are over 40 different adenovirus varieties, some of which cause respiratory disease), adeno-associated virus (AAV, a parvovirus that contains single stranded DNA), or retrovirus (any virus in the family Retroviridae that has RNA as its nucleic acid and uses the enzyme reverse transcriptase to copy its genome into the DNA and integrate into the host cell's chromosome).

The process of delivering a nucleic acid to a cell has been commonly termed transfection or the process of "transfecting" and also it has been termed "transformation." The term transfecting as used herein refers to the introduction of foreign DNA into cells. The nucleic acid could be used to produce a change in a cell that can be therapeutic. The delivery of nucleic acid for therapeutic and research purposes is commonly called "gene therapy." The delivery of nucleic acid can lead to modification of the genetic material present in the target cell. The term "stable transfection" or "stably transfected" generally refers to the introduction and integration of foreign nucleic acid into the genome of the transfected cell. The term "stable transfectant" refers to a cell which has stably integrated foreign nucleic acid into the genomic DNA. Stable transfection can also be obtained by using episomal vectors that are replicated during the eukaryotic cell division (e.g., plasmid DNA vectors containing a papilloma virus origin of replication, artificial chromosomes). The term "transient transfection" or "transiently transfected" refers to the introduction of foreign nucleic acid into a cell where the foreign nucleic acid does not integrate into the genome of the transfected cell. The foreign nucleic acid persists in the nucleus of the transfected cell. The foreign nucleic acid is subject to the regulatory controls that govern the expression of endogenous genes in the chromosomes. The term "transient transfectant" refers to a cell which has taken up foreign nucleic acid but has not integrated this nucleic acid.

The term "solubility" refers to the quantity of a compound (the solute) that dissolves in a given quantity of solvent to form a saturated solution. A "solution" refers to a homogeneous mixture of a liquid (the solvent) with a gas or solid (the solute). In a solution the molecules of the solute are discrete and mixed with the molecules of the solvent. The solubility of a substance depends on the temperature. The "solubility in water" refers to the solubility of a solute in the solvent water. The solubility of certain detergents, such as lipids, is often described as the "critical micelle concentration" (CMC), which term refers to the concentration of a micelle at which the rate of increase of electrical conductance with increase in concentration levels off or proceeds at much slower rate. The term "micelle" refers to a colloidal aggregate of a unique number of amphipatic molecules. The CMC for dipalmitoylphosphatidylcholine has been determined to be approximately $4.7 \times 10^{-10}$ M. Shorter chain lipids have a higher solubility, and thus stronger detergent activity. For instance, the CMC for dicaproylphosphatidylcholine is approximately $1 \times 10^{-2}$ M; the CMC for cholesterol is approximately $2 \times 10^{-8}$ M.

The term "acyl" refers to a radical produced from an organic acid by removal of the hydroxyl group. Chain length ranges from one hydrogen atom to 50 carbon atoms. The hydrocarbon chain can be linear or branched, saturated or unsaturated with one or more double bonds. Examples of acyl radicals include acetyl, pentanoyl, palmitoyl, stearoyl, myristoyl, caproyl and oleoyl.

The term "wax" refers to a variety of solid and semi-solid substances. Mineral waxes are mixtures of hydrocarbons with high molecular weights. Waxes found in animals or plants are mainly esters of fatty acids. "Fatty acids" refers to compounds consisting of a hydrocarbon chain and a terminal carboxyl group. Chain length ranges from one hydrogen atom (methanoic acid) to 30 carbon atoms. The hydrocarbon chains can be linear or branched, saturated or unsaturated with one or more double bonds. As chain length increases, melting points are raised and water solubility decreases. Unsaturation and branching tend to lower melting points. "Lipids" refers to two groups of compounds: 1) complex lipids consisting of esters of fatty acids, including glycerides, glycolipids, phospholipids, and waxes; and 2) simple lipids which do not contain fatty acids, such as steroids, sterols, and terpenes. Examples of simple lipids include corticosteroids, androgens, estrogens, bile acids, cholesterol, and vitamins A, D, E, and K. Lipids can combine with proteins to form "lipoproteins" and with polysaceharide to form "lipopolysaccharides."

The term "cationic lipid" refers to any of a number of lipid species which carry a net positive charge at physiological pH. Such lipids include, but are not limited to, 1,4-bis(3-oleoylamidopropyl) piperazine, DODAC, DOTMA, DDAB, DOTAP, DC-Chol, and DMRIE. Additionally, a number of commercial preparations of cationic lipid formulations are available which can be used in the present invention. These include, for example, LIPOFECTIN (comprising DOTMA and DOPE, from LifeTechnologies, Grand Island, N.Y., USA); LIPOFECTAMINE (comprising DOSPA and DOPE, from LifeTechnologies); CellFectin (comprising TM-TPS and DOPE, Life Technologies); and Insectin-Plus (Invitrogen, Carlsbad, Calif).

The term "detergent" generally refers to any compound that increases the solubility of nonpolar compounds in water. For the purposes of this invention, detergent also refers to any compound that can form mixed micelles or can solubilize a biological membrane. In "anionic detergents" the active part has a net negative charge. Examples of anionic detergents include octanedecanoate (soap) and dodecylbenzenesulphonate. In "cationic detergents" the active part has a net positive charge. Examples of cationic detergents include amines. "Nonionic detergents" have nonionic polar groups as the active pan. Examples of nonionic detergents include Triton, CHAPS, CHAPSO, acylglucoside, Brij. Amphipatic compounds, such as small peptides (e.g., melittin), can also have detergent activity. For the purposes of this invention, non-cationic lipids, and neutral lipids with acyl chain lengths less than $C_{18}$, are classified as detergents.

The term "amphipathic compound" refers to any suitable material containing both hydrophobic and hydrophilic moieties or regions. A subgroup of such compounds comprises "lipids." Hydrophilic characteristics derive from the presence of phosphato, carboxylic, sulfato, amino, sulfhydryl, nitro, carbohydrate, and other like groups. Hydrophobicity could be conferred by the inclusion of groups that include, but are not limited to, long chain saturated and unsaturated aliphatic hydrocarbon groups and such groups substituted by one or more aromatic, cycloaliphatic or heterocyclic group(s). The preferred amphipathic compounds are phospholipids such as phosphoglycerides. "Phospholipids" are a group of lipids having both phosphate group and one or more acyl groups. "Phosphoglycerides" are based on glycerol, wherein the three hydroxyl groups are esterified with two acyl groups and a phosphate group, which itself may be bound to one of a variety of simple organic groups. The two acyl groups can be identical, of similar length, or different. Representative examples of which include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine. Other compounds, such as sphingolipids, glycosphingolipids, triglycerides, and sterols are also amphipatic compounds.

The term "neutral lipid" refers to any of a number of lipid species that exist either in an uncharged or neutral zwitterionic form at physiological pH. Such lipids include, for example cholesterol, DOPE, DLPE, DLPC, phosphatidylcholines, phosphatidylethanolamines, phosphatidylserines, ceramide, sphingomyelin, cephalin, and cerebrosides.

The term "non-cationic lipid" refers to any neutral lipid as described above as well as anionic lipids. Examples of anionic lipids include, but are not limited to, cardiolipin, phosphatidylserine and phosphatidic acid.

As used herein, the term "sample" is used in its broadest sense. Sample is meant to include a specimen or culture obtained from any source, including biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. These examples are not to be construed as limiting the sample types applicable to the present invention.

The following abbreviations are used herein: DOTAP-halide, N-(1-(2,3-dioleoyloxy)propyl)-N,N,N-trimethylammonium halide, wherein the halide can be F, Cl, Br, I, At; DOTAP-Cl, N-(1-(2,3-dioleoyloxy)propyl)-N,N,N-trimethylammonium chloride; DOTAP-I, N-(1-(2,3-dioleoyloxy)propyl)-N,N,N-trimethylammonium iodide; DOPE, 1,2-sn-dioleoylphoshatidylethanolamine; DLPE, dilauroyl phosphatidylethanolamine; DLPC, dilauroylphosphatidylcholine; DMPE, dimyristoyl phosphatidylethanolamine; DPPE, dipalmitoyl phosphatidylethanolamine; CHAPS, 3-[(cholamidopropyl)dimethylammonio]-1-propanesulfonate; CHAPSO, 3-[(cholamidopropyl)dimethylammonio]-2-hydroxy-1-propanesulfonate; TM-TPS, N,N,N,N-tetramethyl-N,N,N,N-tetrapalmitylspermine; DC-Chol, 3.beta.-(N-(N',N'-dimethylaminoethane)carbamoyl) cholesterol; DDAB, N,N-distearyl-N,N-dimethylammonium bromide; DMRIE, N-(1,2-dimyristyloxyprop-3-yl)-N,N-dimethyl-N-hydroxyethyl ammonium bromide; DODAC, N,N-dioleyl-N,N-dimethylammonium chloride; DOGS, diheptadecylamidoglycyl spermidine; DOSPA, N-(1-(2,3-dioleyloxy)propyl)-N-(2-(sperminecarboxamido)ethyl)-N,N-dimethyl ammonium trifluoroacetate; DOTMA, N-(1-(2,3-dioleyloxy)propyl)-N,N,N-trimethylammonium chloride; ESM, egg sphingomyelin; HEPES, 4-(2-hydroxyethyl)-1-piperazineethanesulfonic acid; PBS, phosphate-buffered saline; EGTA, ethylenebis(oxyethylenenitrilo)-tetraacetic acid.

II. The Invention

The present invention relates to compositions and methods for transferring nucleic acids into cells in vitro and in vivo. The compositions comprise a transfection reagent and one or more detergents. In preferred embodiments, the compositions comprise one or more amphipathic compounds and one or more neutral lipids. In preferred embodiments, the compositions comprise delivery systems providing nucleic acid transfer complexes that transfect cells with high efficiency. The following description discusses certain preferred exemplary embodiments of the present invention. The present invention is not limited to these particular examples.

Polynucleotides have been typically delivered to mammalian cells complexed with liposomes containing amphipathic compounds. The liposomes consist of a bilayer surrounding an aqueous core. The present invention provides methods that can be used to increase the efficiency of transfection reagents. The efficiency of a transfection reagent is here defined as the total amount of nucleic acid that is delivered to the target cells. In preferred embodiments, the efficiency is measured as the expression level of a transferred transgene (e.g., luciferase). In preferred embodiments, the transfection level is also measured as the number of cells that are transfected (e.g., by measuring how many cells are expressing a transferred transgene). This invention can also be used to prepare novel transfection complexes.

In some embodiments of the present invention, high efficiency transfection complexes comprise a delivery system (e.g., a complex comprising amphipathic compounds) and one or more short chain lipids (i.e., lipids with an acyl chain length of less than 16 carbons) or detergents. The present invention is not limited by the nature of the delivery system. However, in preferred embodiments of the present invention, the delivery system comprises liposomes made of the amphipathic compounds and short chain lipids or detergents. These high-efficiency transfection complexes not only provide enhanced tranfections (e.g., higher expression levels and/or high number of cells transfected), but also allow for the transfection of cells that have previously been considered difficult to transfect. Such cells include cells that are maintained at temperatures other than 37° C. (e.g., insect cells), as well as cells, that present physical barriers to transfection (e.g., keratinocytes).

As discussed above the efficiency of transfection reagents can be enhanced by the addition of detergents. The presence of relatively small amounts of detergents can provide a significant increase in the transfection efficiency of a particular reagent. The increase can either be found for many cell types (e.g., cell lines), or for specific types of cells (e.g., insect cells), or for particular cell lines (e.g., NIKS or 293 cells). The optimal detergent and amount of detergent can vary broadly from cell type to cell type and cell line to cell line. The formulation of an optimized transfection reagent for a particular cell type or cell line is accomplished using the assay described in Example 8. In general, the development of a novel, more efficient transfection reagent proceeds through screening of combinations of compounds as disclosed herein. The efficiency of a transfection reagent is generally determined by the amount of expression of the transfected gene (the transgene) that can be measured at a predetermined time following the transfection. The choice of transgene for these experiments is not critical, provided a sufficiently sensitive, accurate, and reproducible assay is available to allow measurements of transgene expression differences between samples transfected with different transfection reagents. Examples of frequently used transgenes for such purposes include luciferase, secreted alkaline phosphatase, green fluorescent protein, and β-galactosidase. Measurement of transgene expression can be performed on cell extracts (e.g., luciferase, β-galactosidase, secreted alkaline phosphatase), cells in situ (e.g., green fluorescent protein, β-galactosidase; measurements made by microscopy or flow cytometry), cells in vitro (e.g., secretion of gene products into the culture medium), or cells in vivo (e.g., secretion of gene products into the blood). Another measure for transfection efficiency is the direct determination of the amount of nucleic acid that is transferred into the target cells.

In developing a novel transfection reagent for a particular cell type or cell line, one would perform a series of transfection in these cells with the objective to identify the reagent that results in the highest transfection efficiency. Transfections are frequently accompanied with toxicity (e.g., cell death, delayed growth). Therefore, a second objective of developing novel transfection reagents is to obtain the lowest toxicity. An ideal reagent would posses both high transfection efficiency and low toxicity properties. However, for specific purposes, one could optimize a reagent for only one of these properties. In typical optimization experiments, a wide variety of detergents (each at several concentrations) are added to several transfection reagents. The reagents are then mixed with nucleic acid and used to transfect the target cells. Following determination of transfection efficiency (and toxicity) for each reagent, a rank order is made. In a second round, several of the best reagents are further optimized by testing addition of similar detergents and testing of a wider range of concentrations. Repetitive rounds of transfection and optimization experiments will yield the desired novel transfection reagent. The quality of optimization is determined in large part by the breadth of compounds tested, the determination of transfection efficiency, and the number of selection rounds. In some cases, several optimal reagents may be developed for specific cell types or cell lines. For example, one reagent could be optimized for the highest possible transfection efficiency, whereas another reagent could be optimized for a reasonable high transfection efficiency with the lowest possible accompanying toxicity. Furthermore, equally efficient reagents may be based on different transfection reagents and detergents. The optimal type and amount of detergent may vary with the transfection reagent used. Multiple detergents can be added to a transfection reagent to optimize its activity.

The present invention provides a process of transfecting a nucleic acid into a cell for expression by associating a selected cell with a transfection reagent, an effective amount of a detergent and a selected nucleic acid, in solution. The result of the process is that the nucleic acid becomes associated with a selected cell. The nucleic acid can be on the membrane of the cell or inside the cytoplasm, nucleus, mitochondria, or other organelles of the cell.

This invention is of particular use for the delivery of a nucleic acid when one wants to study the nucleic acid's effect on a cell. The nucleic acid could also be used to produce a change in a cell that can be therapeutic. This change can be effected when the cell is transplanted back into the animal or person. The delivered nucleic acid could also produce a therapeutic protein or RNA that is then delivered to the animal or person apart from the cell. Transfections are also done to produce viruses or viral vectors that are studied or used for therapeutic, gene therapy purposes. The delivery of nucleic acids or genetic material for therapeutic purposes is commonly called "gene therapy."

III Formulations

Addition of detergents increases the efficiency of a transfection reagent. However, the optimal type and amount of detergent vary for different transfection reagents and target cell types. For instance, experiments conducted during the development of the present invention have determined that the cationic lipid DOTAP is an efficient transfection reagent for insect cells, particularly insect cell lines that can be grown in vitro (e.g., Sf9, Sf21, High Five, S2). In a typical transfection reagent, the DOTAP is mixed with a neutral lipid (e.g., DOPE, cholesterol) to form a liposome. Addition of any of a number of detergents proved to significantly enhance the transfection efficiency of this reagent for transfecting insect cells. Yet, for transfecting Sf9 cells, addition of neutral lipids with acyl chain lengths between 8 and 16 (e.g., DLPE, DLPC) proved more efficient than addition of CHAPS. Optimal enhancement with DLPE was obtained over a range of 1–10% (weight percentage of total composition of DOTAP, DOPE, and neutral lipid).

IV. Methods of Use

A. A Process of Delivering a Biologically Active Substance to a Cell

The present invention provides a process of delivering a biologically active substance to a cell. In accordance with that process, a target cell (a cell to which the substance is to be delivered) is exposed to the biologically active substance in the presence of a delivery system of the present invention. Preferred such delivery systems are the same as set forth above. A target cell can be located in vitro (e.g., cell culture) or in vivo (e.g., in a living organism).

As used herein, the phrase "biologically active substance" means any substance having the ability to alter the function of a living cell, tissue or organism. A biologically active substance can be a drug or other therapeutic agent. A biologically active substance can also be a chemical that interacts with and alters the function of a cell. By way of example, a biologically active substance can be a protein or peptide fragment thereof such as a receptor agonist or antagonist. In addition, a biologically active substance can be a nucleic acid.

Where the target cell is located in vitro, the biologically active substance, and the delivery system are typically added to the culture medium in which the cell is being cultured. The active substance and delivery system can be added to the medium either simultaneously or sequentially. Alternatively, the biologically active substance and the delivery system can be formed into a complex and then added to the medium. A complex between a biologically active substance and a delivery system of the present invention can be made by contacting those materials under appropriate reaction conditions. Means for making such complexes are set forth hereinafter in the Examples.

Where the target cell is located in vivo, the biologically active substance and the delivery system are typically administered to the organism in such a way as to distribute those materials to the cell. The materials can be administered simultaneously or sequentially as set forth above. In one embodiment, the biologically active substance and the delivery system are administered as a complex. The delivery system and biologically active substance can be infused into the cardiovascular system (e.g., intravenously, intraarterially), injected directly into tissue containing the target cell (e.g., intramuscularly), or administered via other parenteral routes well known to one skilled in the art.

B. Process of Transfecting a Cell with a Nucleic Acid

Despite remarkable accomplishments in cloning genes relevant to many diseases, there remains to be solved the challenging problem of efficiently transferring and stably expressing nucleic acids such as transgenes in appropriate cells and tissues. Several new methods of gene transfer into postnatal somatic tissue are under development in many laboratories. They can be divided into two general approaches: those using direct transfer into cells in vivo and those using indirect methods involving the re-implantation of genetically-modified cells.

The currently-available transfection reagents (almost always based on cationic lipids) can mediate gene transfer with variable efficiency in vitro, but relatively poorly in vivo. The present invention provides a process of improving the transfection efficiency of transfection reagents. This is accomplished by the addition of a detergent. The transfection reagent-detergent mixture can be formulated prior to complexation with nucleic acids. Following this approach a novel transfection reagent is created, which can be manufactured to generally accepted quality control parameters. The resulting reagents can be sold as general transfection reagents (e.g., in kits), or as transfection reagents optimized for specific cell types. Alternatively, the detergent can be added while forming the nucleic acid-transfection reagent complex, or even following formation of this complex. The detergent can therefore be marketed as a transfection reagent enhancer. Details of formulating transfection reagents with detergents according to the present invention are set forth hereinafter in the Examples.

Not only can a process of the present invention be used to transfect a cell, but the transfection is shown to result in a marked increase in the expression of the transfected nucleic acid (See Examples, hereinafter). Thus, a delivery system of the present invention has use in a process of increasing nucleic acid expression in a cell.

Experimental

The following examples are provided in order to demonstrate and further illustrate certain preferred embodiments and aspects of the present invention and are not to be construed as limiting the scope thereof.

EXAMPLE 1

Preparation of Liposome Formulations

This example describes the preparation of liposome formulations in some preferred embodiments of the present invention. Liposomes were prepared by mixing chloroform or ethanol solutions of the different lipids in microcentrifuge tubes and removing the solvent by nitrogen gas flow to produce dried lipid films. Tubes were placed under vacuum overnight to remove solvent traces. The amounts of cationic lipids in all cases were 1 mg with different amounts of other lipids as specified. One ml of sterile water or 10 mM HEPES buffer, pH 7.8, was added, and the tubes were sealed and vortexed for 1 min at room temperature and sonicated to obtain a clear emulsion. Compositions were stored at 4° C. A liposome formulation consisting of DOTAP, DOPE, and DLPE, in a ratio of 10:9:1 (w:w:w), and prepared as described above, is referred to herein as TRANSIT-INSECTA. The molar ratio for this preparation is 14.85:12.11:1.73 (DOTAP:DOPE:DLPE).

For larger scale production, liposomes were prepared by mixing chloroform solutions of the different compounds in a glass vial. The amounts of cationic lipids in all cases were 1 mg/ml with different amounts of other lipids as specified. The solution was then dispensed in 1 ml aliquots in 2 ml microcentrifuge tube. Tubes were placed in the speed vacuum until the compounds were thoroughly dried. One ml of sterile water was added to each tube, and the tubes were capped and vortexed for 1 min at room temperature. Compositions were stored at 4° C. overnight, and then sonicated 5 minutes. The reagent was then removed from each microcentrifuge tube and pooled into a 50 ml conical tube and stored at 4° C. until use.

EXAMPLE 2

Cell Culture

A. Cell Preparation and Transfection

This example describes the preparation, maintenance, and transfection of cells with the transfection complexes of the present invention. The following mammalian cell lines were used: mouse 3T3 fibroblasts, 293 (monkey kidney cell line transformed with the adenovirus E1 gene), and BNL (mouse hepatocytes) were all maintained in Dulbeco's Modified MEM media supplemented with 10% fetal calf serum. All mammalian cell cultures were maintained in a humidified atmosphere of 5% $CO_2$ in air at 37° C. Several insect cell lines were used: Sf9 and Sf21 (*Spodoptera frugiperda* pupal ovarian cells) cells were maintained in TC-100 medium, and High Five or BTI-TN-5BI-4 (*Trichoplusia ni* embryonic ovarian cells) cells were maintained in Ex-Cell medium at 27° C. in an atmosphere of 5% $CO_2$ in air. S2 (*Drosophila melanogaster* embryonic cells) were maintained in Shields and Sang M3 medium supplemented with 5% FCS at 25° C. The cells were seeded in a 6-well plate (35 mm culture dishes) 24 h before the transfection at 70% confluence. Before transfection, the cells were washed once or twice with serum-free medium, and placed in 2 ml serum-free medium per 35-mm dish. The liposomes were diluted in 0.15 ml of serum-free medium. Following a 5 minute incubation at room temperature, two μg of plasmid DNA (containing the luciferase or β-galactosidase reporter genes described below) was added, followed by a 5 minute incubation at room temperature prior to being added to the cells in the culture dish. The cells were incubated under the appropriate conditions. After four hours, the transfection mixture was removed and replaced with 2 ml of regular culture medium. The cultures were incubated for 48 hours until they were harvested for analysis of their reporter gene expression. Transfections with commercially available reagents were also prepared according to the manufacturers' recommendations.

B. Use of Reporter Genes

The firefly luciferase and *E. coli* β-galactosidase reporter genes were used to determine the efficiency of DNA transfer quantitatively. The previously described plasmid DNA pCI-Luc$_+$ was used to express the firefly luciferase reporter gene from the human cytomegalovirus (CMV) promoter. The β-galactosidase expression plasmid, pIE1HR5/LacZ expresses β-galactosidase under the transcriptional control of the baculovirus IE1HR5 promoter/enhancer.

C. Reporter Gene Assays

For determination of luciferase activity, cells were lysed by the addition of 200 μl of lysis buffer (0.1% Triton X-100, 0.1 M K-phosphate, 1 mM DTT, pH 7.8). Ten μl of the cellular extract were analyzed for luciferase activity, using the Enhanced Luciferase Assay kit (Mirus). For determination of β-galactosidase activity, the cells were lysed by the addition of 200 μl of lysis buffer (0.1% Triton X-100, 0.1 M K-phosphate, 1 mM DTT, pH 7.8). β-Galactosidase activity was determined using a chemiluminescent assay (Tropix).

EXAMPLE 3

Transfection of Sf9 Cells

Figure 1:
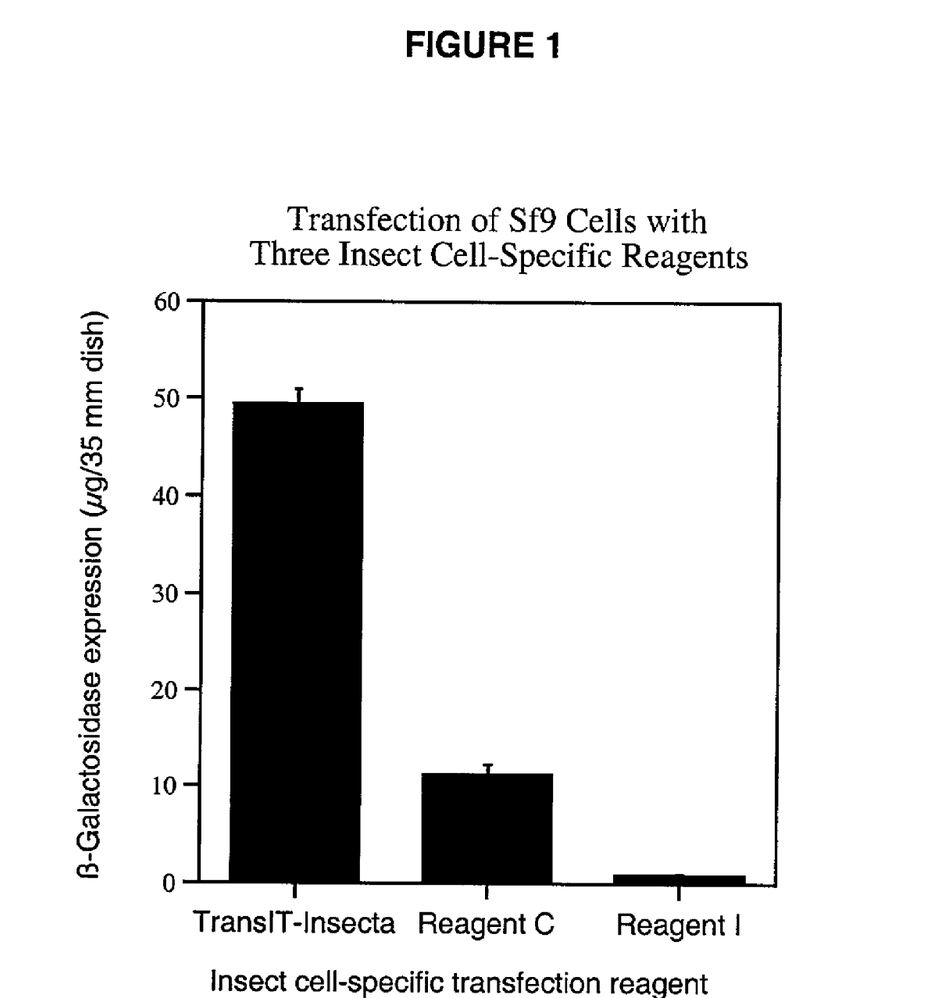
FIG. 1 shows data from the transfection of Sf9 cells with three insect-cell specific reagents.

Two μg of the β-galactosidase expression vector pIE1HR5/LacZ were transfected into Sf9 cells using TRAN-SIT-INSECTA, Reagent C (CELLFECTIN from Life Technologies) and Reagent I (INSECTIN-PLUS from Invitrogen). Transfections were performed in serum free medium in 35-mm dishes in triplicate. Cells were seeded one day prior to transfection. For each reagent, the optimal protocol as suggested by the manufacturer was used. Medium was refreshed 4 hours after transfection. Reporter gene expression was determined after 2 days using a chemiluminescent assay (Tropix). The results are shown in FIG. 1, demonstrating that the transfection complexes of the present invention produced significantly higher expression than the other transfection reagents.

EXAMPLE 4

Comparison of Different Reagents for Transfecting Sf9 Cells

Figure 2:
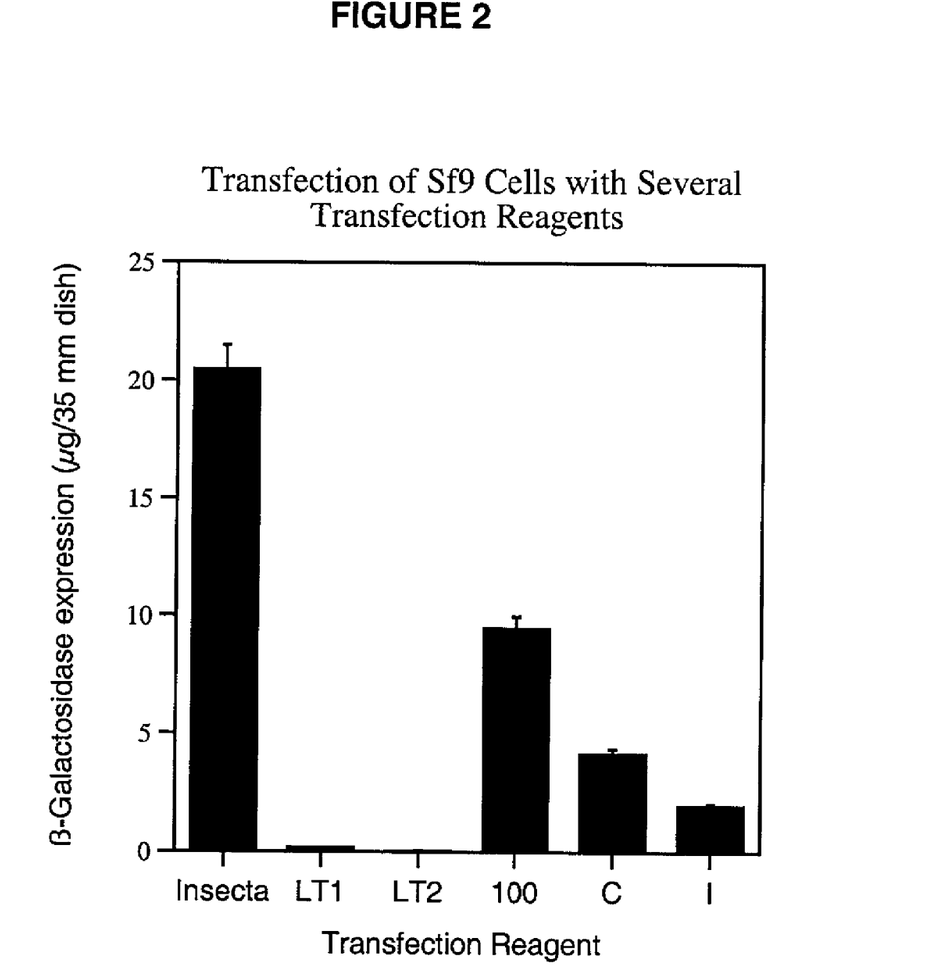
FIG. 2 shows data from the transfection of Sf9 cells with several transfection reagents.

Two μg of the β-galactosidase expression vector pIE1HR5/LacZ were transfected into Sf9 cells using the following reagents: TRANSIT-INSECTA; LT1, LT2, and 100 (TransIT-LT1, -LT2, and -100, respectivelty from Mirus Corporation); Reagent C (CELLFECTIN from Life Technologies); and Reagent I (INSECTIN-PLUS from Invitrogen). Transfections were performed in serum free medium in 35-mm dishes in triplicate. Cells were seeded one day prior to transfection. For each reagent, the optimal protocol as suggested by the manufacturer was used. Medium was refreshed 4 hours after transfection. Reporter gene expression was determined after 2 days using a chemiluminescent assay (Tropix). The results are shown in FIG. 2, demonstrating that the transfection complexes of the present invention produced significantly higher expression than the other transfection reagents.

EXAMPLE 5

Transfection of HIGH FIVE Cells

Figure 3:
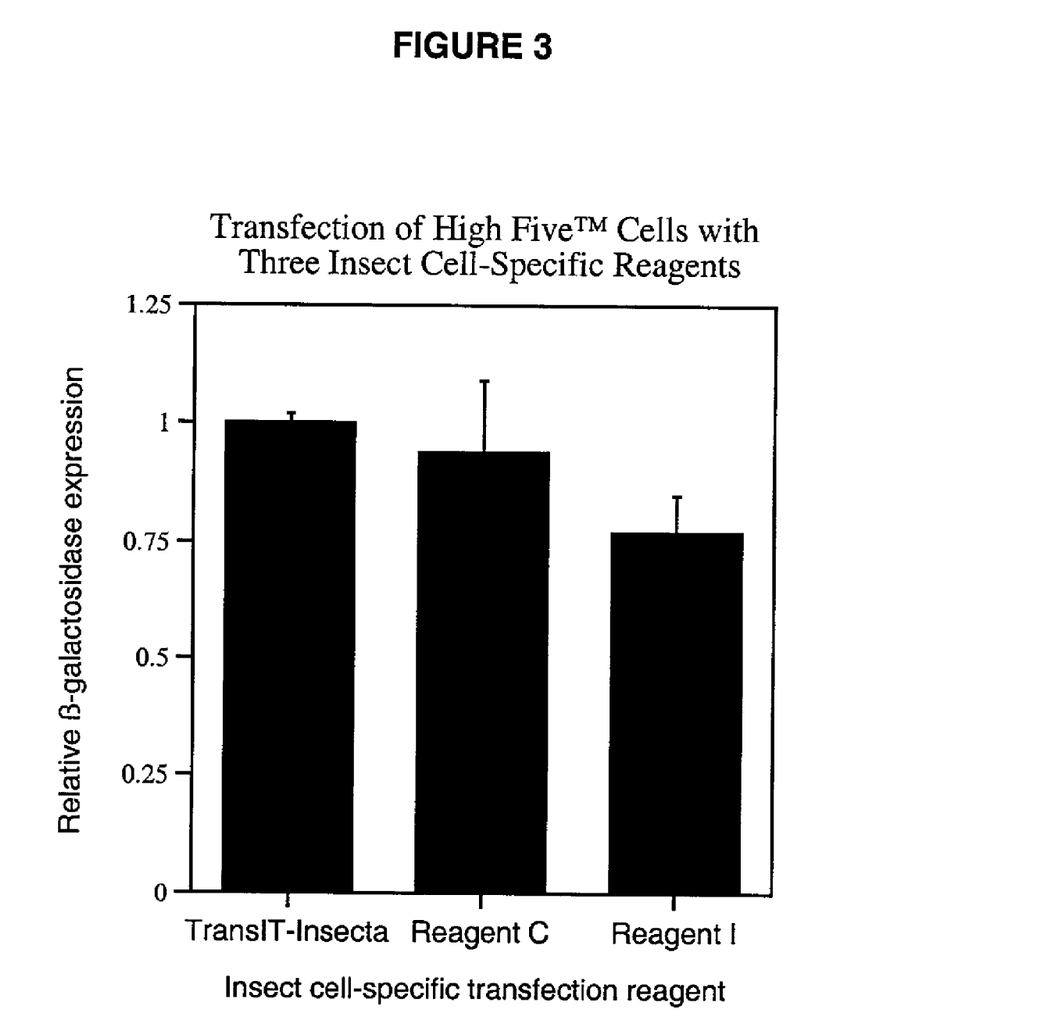
FIG. 3 shows data from the transfection of HIGH FIVE cells with three insect-cell specific reagents.

Two μg of the β-galactosidase expression vector pIE1HR5/LacZ were transfected into HIGH FIVE (invitrogen)cells using TRANSIT-INSECTA,reagent C (CELL-FECTIN from Life Technologies) and Reagent I (INSEC-TIN-PLUS from Invitogen). Transfections were performed in serum free medium in 35-mm dishes in triplicate. Cells were seeded one day prior to transfection. For each reagent, the optimal protocol as suggested by the manufacture was used. Medium was refreshed 4 hours after transfection. Reporter gene expression was determined after 2 days using a chemiluminescent assay (Tropix). The results are shown in FIG. 3.

EXAMPLE 6

Transfection of Sf21 Cells

Figure 4:
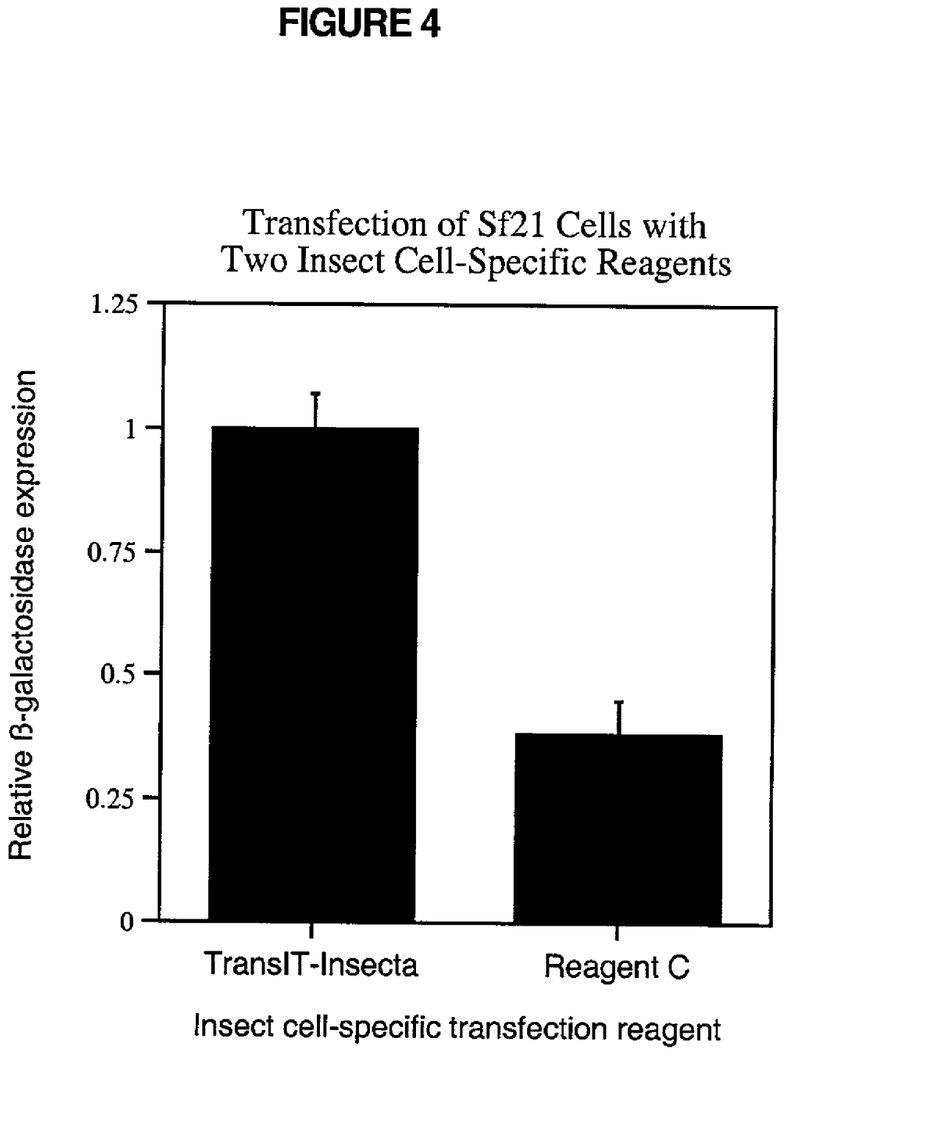
FIG. 4 shows data from the transfection of Sf21 cells with two insect-cell specific transfection reagents.

Two μg of the β-galactosidase expression vector pIE1HR5/LacZ were transfected into Sf21 cells using TRANSIT-INSECTA and Reagent C (CELLFECTIN from Life Technologies). Transfections were performed in serum free medium in 35-mm dishes in triplicate. Cells were seeded one day prior to transfection. For each reagent, the optimal protocol as suggested by the manufacturer was used. Medium was refreshed 4 hours after transfection. Reporter gene expression was determined after 2 days using a chemiluminescent assay (Tropix). The results are shown in FIG. 4, demonstrating that the transfection complexes of the present invention produced significantly higher expression than the other transfection reagents.

EXAMPLE 7

Preparation of TransIT-LT Based Transfection Reagents

The commercially available transfection reagent TransIT-LT1 (Mirus Corporation, Madison, Wis.) consists of a formulation of the amphipatic compound 1,4-bis(3-oleoylamidopropl) piperazine and histone H1, wherein the ratio of 1,4-bis(3-oleoylamidopropyl) piperazine to histone H1 is 3 to 1 (w:w). Novel, cell type or cell line specific reagents are prepared by addition of detergents to TransIT-LT1. For instance, TransIT-Keratinocyte is prepared by addition of 2.08 mg of DLPE (Sigma) to 50 ml of TransIT-LT1; TransIT-LT293 is prepared by addition of 4.175 mg CHAPS (Sigma) to 50 ml of TransIT-LT1.

EXAMPLE 8

Optimization of Transfection Reagents

Transfection reagents are optimized by testing a large number of transfection reagent/detergent combination in transfection experiments using the cells (cell lines) of interest. The criterium for enhanced gene transfer usually consists of increased expression of a reporter gene. For instance, luciferase expression can be determined in cell extracts 1 or 2 days following transfection. Another measure for the transfection efficiency can be the percentage of cells expressing the transfected gene. For instance, cells transfected with the LacZ gene can be stained blue using the substrate X-Gal. Transgene expression can also be determined by flow cytometric analysis, providing information on the expression level in each analyzed cell. In a typical optimization experiment, several different detergent are added to small aliquots a transfection reagent (at different composition ratios). The resulting novel transfection reagents are then mixed with plasmid DNA and used for transfection of the target cells. Following analysis of transgene expression, the best performing reagents can be further optimized by testing a wider range of ratios, by testing similar transfection reagents, and similar detergents. The exact method of formulation depends on the nature of the transfection reagent. Whereas detergent can generally be added to the readily available transfection reagent TransIT-LT1 (see example 7), other combination may require specialized preparation methods. For instance, liposomal transfection reagents typically require the detergent to be included during the preparation of the liposomes. This can be accomplished by mixing the individual components of the liposome, including the detergent, drying the components, followed by resuspension and liposome formation (typically accomplished by sonication). An example of such a procedure is provided in Example 1. Specific conditions required for certain cell lines, transgenes, transfection reagents, and detergents may be applied, as known in the art for the system with which the present invention is being applied. Examples of optimization experiments are presented in Examples 9–13. Other approaches for identifying efficient transfection reagents are known including massive screening of many formulations (e.g., using high throughput screening), or rational design.

EXAMPLE 9

Transfection of 293 Cells

HEK-293 cells were maintained in Minimum Essentials Medium (Sigma) with 10% Horse Serum (HyCLONE). Cells were maintained in a humidified atmosphere of 5% $CO_2$ in air at 37° C. Cells were seeded in a 6-well plate (35 mm culture dishes) 24 hours before transfection. Transfection reagent was diluted in 150 µl of serum-free medium and incubated for 5 minutes at room temperature. Two µg of the luciferase expression vector pCI-Luc$^+$ was added and incubated at room temperature for 5 minutes. The complexes were then added to the cells in the 35 mm wells in their complete medium and mixed. The ratio of TransIT-LT1 to pDNA was always 3:1. Transfections were performed in regular growth medium in 35-mm dishes in triplicate. Reporter gene expression was determined after 2 days using a chemiluminescent assay (Mirus Corporation). For comparison, 293 cells were also transfected with TransIT-LT1. The results are shown in the Table, demonstrating that certain transfection complexes of the present invention with detergent added to TransIT-LT1 produced significantly higher gene expression.

| Reagent (ratio detergent:pDNA) | Luciferase expression (in relative light units) | | | | | | |
|---|---|---|---|---|---|---|---|
| TransIT-LT1 | 4.63E+09 | 5.90E+09 | 1.54E+10 | 2.38E+10 | 4.99E+09 | 1.30E+10 | 1.79E+10 |
| DLPE (0.25:1) | | | | | 7.34E+09 | | 1.87E+10 |
| DLPE (0.5:1) | | | | | 7.83E+09 | | |
| DPPE (1:1) | | | 1.55E+10 | 2.44E+10 | | | |
| CHAPS (0.25:1) | | | | 2.68E+10 | | | |
| CHAPS (0.5:1) | | 5.90E+09 | | | | 1.45E+10 | |
| CHAPS (1:1) | | | | | 6.82E+09 | | |
| CHAPS (2:1) | | | | | 7.37E+09 | | |
| CHAPSO (0.5:1) | | | | 2.65E+10 | | | |
| CHAPSO (1:1) | | | | 2.61E+10 | | | |
| Cholesterol (0.125:1) | 5.37E+09 | 6.93E+09 | | | 5.92E+09 | 1.33E+10 | |
| Cholesterol (0.25:1) | | | | | 6.34E+09 | 1.41E+10 | |
| Cholesterol (0.5:1) | | | | | | 1.44E+10 | |
| Deoxycholic acid (0.25:1) | | | | 2.61E+10 | | | |
| Deoxycholic acid | | | | 2.77E+10 | | | |

-continued

| | | | | |
|---|---|---|---|---|
| (0.5:1) | | | | |
| DOPE (0.5:1) | | 2.49E+10 | | |
| Lithocholic acid (0.5:1) | | | | |
| Lithocholic Acid (1:1) | | | | |
| Cholic acid (0.25:1) | | | | |
| Cholic acid (0.5:1) | | | | |
| Cholic acid (1:1) | | | | |
| Cholic acid methyl ester (0.5:1) | | | | |
| Cholic acid methyl ester (1:1) | | | | |

| Reagent (ratio detergent:pDNA) | Luciferase expression (in relative light units) | | | |
|---|---|---|---|---|
| TransIT-LT1 | 1.24E+10 | 1.31E+10 | 2.09E+10 | 2.67E+10 |
| DLPE (0.25:1) | | | | |
| DLPE (0.5:1) | | | | |
| DPPE (1:1) | | | | |
| CHAPS (0.25:1) | | 1.79E+10 | 2.25E+10 | |
| CHAPS (0.5:1) | | 1.62E+10 | 2.23E+10 | 3.07E+10 |
| CHAPS (1:1) | | | | 2.93E+10 |
| CHAPS (2:1) | | | | |
| CHAPSO (0.5:1) | | | | |
| CHAPSO (1:1) | | | | |
| Cholesterol | | | | |
| Cholesterol Cholesterol (0.5:1) | | | | |
| Deoxycholic acid (0.25:1) | | 1.68E+10 | 2.57E+10 | |
| Deoxycholic acid (0.5:1) | | | 2.32E+10 | |
| DOPE (0.5:1) | | | | |
| Lithocholic acid (0.5:1) | 1.37E+10 | | | |
| Lithocholic Acid (1:1) | 1.34E+10 | | | |
| Cholic acid (0.25:1) | | 1.51E+10 | | |
| Cholic acid (0.5:1) | 1.35E+10 | 1.82E+10 | | |
| Cholic acid (1:1) | 1.28E+10 | | | |
| Cholic acid methyl ester (0.5:1) | 1.37E+10 | | | |
| Cholic acid methyl ester (1:1) | 1.36E+10 | 1.58E+10 | | |

EXAMPLE 10

Transfection of 293 Cells

Two μg of the luciferase expression vector pCI-Luc$^+$ were transfected into 293 cells using mixtures of the transfection reagent TRANSIT-LT1 (Mirus Corporation) and CHAPS. Transfections were performed in regular growth medium in 35-mm dishes in triplicate. Cells were seeded one day prior to transfection. Reporter gene expression was determined after 2 days using a chemiluminescent assay (Mirus Corporation). A commercial reagent under the trade name TransIT-293 is available (Mirus Corporation), with a composition of TRANSIT-LT1 with 0.0835 mg CHAPS added per ml reagent. The results are shown in the Table, demonstrating that the transfection complexes of the present invention with CHAPS added to TRANSIT-LT1 produced significantly higher gene expression.

| | Reagent | | | | |
|---|---|---|---|---|---|
| | LT1 | LT1+CHAPS | LT1+CHAPS | H1:58(2.5:1)+ CHAPS | TransIT-293 batch #1108 |
| Ratio LT1:CHAPS:pDNA (v:w:w) | (3:1:0) | (3:0.25:1) | (3:0.5:1) | (3:0.25:1) | (3:0.25:1) |
| Experiment 1 | 2.38E+10 | 2.68E+07 | 2.22E+10 | | |
| Experiment 2 | 8.60E+09 | 1.01E+10 | 1.02E+10 | | |
| Experiment 3 | 6.17E+09 | 7.80E+09 | 9.34E+09 | | |
| Experiment 4 | 7.97E+09 | 8.89E+09 | | | 8.10E+09 |

-continued

| | Reagent | | | | |
|---|---|---|---|---|---|
| | LT1 | LT1+CHAPS | LT1+CHAPS | H1:58(2.5:1)+ CHAPS | TransIT-293 batch #1108 |
| Experiment 5 | 2.02E+10 | | | | 2.23E+10 |
| Experiment 6 | 2.73E+09 | 3.53E+09 | | 3.70E+09 | |
| complexed together | | 3.18E+09 | | 3.78E+09 | |

EXAMPLE 11

Culture and Transfection of NIKS Cells

Primary human keratinocytes (NIKS cells, Stratatech) were maintained in EpiLife media (Cascade Biologics). The cells were maintained in a humidified atmosphere of 5% $CO_2$ in air at 37° C. The cells were seeded in a 6-well plate (35 mm culture dishes) 24 hr before the transfection at approximately 300,000 cells per ml. TransIT-LT1 or TransIT-Keratinocyte (see example 7) reagent was diluted in 150 µl of serum-free medium and incubated for 5 minutes at room temperature. Then 2 µg of plasmid DNA was added and incubated at room temperature for 5 minutes. The complexes were then added to the cells in the 35 mm wells in their complete medium and mixed. The cells were incubated for 24 hours with no media change. The table shows data from three experiments to optimize the ratio of TransIT-Keratinocyte (TransIT-K) to plasmid DNA. For comparison, transfection results with TransIT-LT1 are shown. From these results, it is clear that TransIT-Keratinocyte reagent transfects NIKS cells with much higher efficiency.

| Reagent (ratio reagent:pDNA) | Luciferase expression (relative light units) |
|---|---|
| TransIT-LT1 (3:1) | 4.02E+06 |
| TransIT-K (3:1) | 1.34E+07 |
| TransIT-K (4:1) | 6.88E+06 |
| TransIT-LT1 (3:1) | 3.42E+07 |
| TransIT-K (3:1) | 1.26E+08 |
| TransIT-K (4:1) | 5.52E+07 |
| TransIT-LT1 (3:1) | 2.65E+06 |

-continued

| Reagent (ratio reagent:pDNA) | Luciferase expression (relative light units) |
|---|---|
| TransIT-K (2:1) | 1.61E+07 |
| TransIT-K (3:1) | 2.23E+07 |
| TransIT-K (4:1) | 3.63E+07 |
| TransIT-K (5:1) | 3.34E+07 |
| TransIT-K (6:1) | 1.72E+07 |

EXAMPLE 12

Transfection of Jurkat Cells

Jurkat cells were maintained in RPMI1640 medium (Sigma) with 10% fetal calf serum (Hyclone) and grown in a humidified incubator at 37° C. in an atmosphere of 5% CO2 in air. Two µg of the luciferase expression vector pCI-Luc$^+$ were transfected into Jurkat cells using mixtures of the transfection reagent TRANSIT-LT1 (Mirus Corporation) and detergents. The ratio of TRANSIT-LT1 to pDNA was always 3:1. Transfections were performed in regular growth medium in 35-mm dishes in triplicate. Cells were seeded one day prior to transfection. Reporter gene expression was determined after 2 days using a chemiluminescent assay (Mirus Corporation). For comparison, Jurkat cells were also transfected with TransIT-LT1. The results are shown in the Table, demonstrating that certain transfection complexes of the present invention with detergent added to TRANSIT-LT1 produced significantly higher gene expression.

| Reagent (ratio detergent:pDNA) | Luciferase expression (relative light units) | | | | | | |
|---|---|---|---|---|---|---|---|
| TransIT-LT1 | 3.40E+07 | 2.73E+07 | 4.06E+07 | 2.82E+07 | 1.70E+06 | 9.79E+05 | 1.27E+06 |
| DLPE (0.25:1) | | | | | 2.78E+06 | 1.40E+06 | |
| DLPE (0.5:1) | | | | | 3.23E+06 | | |
| DMPE (0.25:1) | 3.78E+07 | | | | | | |
| DPPE (0.5:1) | 4.10E+07 | | | 3.03E+07 | 2.21E+06 | | |
| CHAPS (0.125:1) | | 4.86E+07 | | | | | |
| CHAPS (0.25:1) | | 4.81E+07 | | | | | 2.65E+06 |
| CHAPS (0.5:1) | | 4.11E+07 | | | | | 2.15E+06 |
| CHAPSO (0.25:1) | | 3.85E+07 | 4.47E+07 | | | | |
| CHAPSO (0.5:1) | | 3.31E+07 | | | | | |
| Cholesterol (0.125:1) | | 3.33E+07 | | | | | |
| Cholesterol (0.25:1) | | 4.28E+07 | | | | | |
| Cholesterol (0.5:1) | | 4.74E+07 | | 7.08E+07 | | | 1.53E+06 |
| Deoxycholic acid (0.25:1) | | | 4.25E+07 | | | | 2.05E+06 |
| Deoxycholic acid (0.5:1) | | | 5.64E+07 | | 2.71E+06 | | |

| Reagent (ratio detergent:pDNA) | Luciferase expression (relative light units) | | |
| --- | --- | --- | --- |
| Deoxycholic acid (1:1) | 6.39E+07 | 4.06E+07 | 1.87E+06 |
| DOPE (0.25:1) | 4.32E+07 | | |
| DOPE (0.5:1) | 3.04E+07 | | |

EXAMPLE 13

Transfection of COS7 Cells

COS7 cells were maintained in DMEM medium (Sigma) with 10% fetal calf serum (Hyclone) and grown in a humidified incubator at 37° C. in an atmosphere of 5% CO2 in air. Two μg of the luciferase expression vector pCI-Luc$^+$ were transfected into COS7 cells using mixtures of the transfection reagent TRANSIT-LT1 (Mirus Corporation) and detergents. The ratio of TRANSIT-LT1 to pDNA was always 3:1. Transfections were performed in regular growth medium in 35-mm dishes in triplicate. Cells were seeded one day prior to transfection. Reporter gene expression was determined after 2 days using a chemiluminescent assay (Mirus Corporation). For comparison, Jurkat cells were also transfected with TransIT-LT1. The results are shown in the Table, demonstrating that certain transfection complexes of the present invention with detergent added to TRANSIT-LT1 produced significantly higher gene expression.

EXAMPLE 14

Synthesis of DOTAP-Cl

To a solution of 3-(dimethylamino)-1,2-propanediol (1.08 g, 9.04 mmol) in 1,4-dioxane (35 ml) was added oleoyl chloride (7.50 ml, 22.6 mmol, freshly distilled) drop wise, followed by N,N-diisopropylethylamine (3.94 ml, 22.6 mmol). The solution was heated at 60° C. for 22 hours and then cooled to room temperature and filtered. Methyl iodide (0.85 ml, 13.6 mmol) was added followed by N,N-diisopropylethylamine (2.36 ml, 13.6 mmol). The solution was heated at 60° C. for 16 hours and then cooled to room temperature. The solution was concentrated under reduced pressure, and resulting solid was crystallized twice from dry acetonitrile to afford 5.84 g (82%) DOTAP-I as a white solid ($^1$H NMR, MS 663 M$^+$).

DOTAP-I (2.70 g, 3.42 mmol) was taken up in methanol/dichloromethane (10 ml, 8:2) and loaded onto Dowex 22Cl anion exchange resin (2.0×17.0 cm, methanol/dichlo-

| Reagent (ratio detergent:pDNA) | Luciferase expression (relative light units) | | | | |
| --- | --- | --- | --- | --- | --- |
| TransIT-LT1 | 5.21E+09 | 1.17E+10 | 7.35E+09 | 2.01E+10 | 1.79E+10 |
| DLPE (0.125:1) | | | 1.22E+10 | 2.14E+10 | 2.10E+10 |
| DLPE (0.25:1) | | | 1.15E+10 | 2.45E+10 | 2.07E+10 |
| DLPE (0.5:1) | | | | 2.23E+10 | |
| CHAPS (0.125:1) | 6.78E+09 | 1.54E+10 | | | |
| CHAPS (0.25:1) | 7.86E+09 | 1.70E+10 | | | |
| CHAPS (0.5:1) | 7.92E+09 | 1.93E+10 | | | |
| CHAPS (1:1) | 5.81E+09 | 1.60E+10 | | | |
| CHAPS (2:1) | 6.38E+09 | | | | |
| CHAPSO (0.125:1) | | 1.24E+10 | | | |
| CHAPSO (0.25:1) | | 1.53E+10 | | | |
| CHAPSO (0.5:1) | | 1.56E+10 | | | |
| CHAPSO (1:1) | | 1.98E+10 | | | |
| Cholesterol (0.125:1) | 8.21E+09 | 2.03E+10 | 9.52E+09 | 2.20E+10 | |
| Cholesterol (0.25:1) | 9.10E+09 | 1.93E+10 | | | |
| Cholesterol (0.5:1) | 7.85E+09 | 1.48E+10 | 1.42E+10 | | 2.02E+10 |
| Deoxycholic acid (0.125:1) | | 1.84E+10 | | | |
| Deoxycholic acid (0.25:1) | 9.02E+09 | 1.68E+10 | | | |
| Deoxycholic acid (0.5:1) | | 1.77E+10 | | | |
| Deoxycholic acid (1:1) | | 1.28E+10 | | | |
| Deoxycholic acid (2:1) | | 1.40E+10 | | | |
| DOPE (0.25:1) | 7.80E+09 | | | | |
| DOPE (0.5:1) | 6.10E+09 | | | | |
| DOPE (1:1) | 6.82E+09 | | | | |
| DOPE (2:1) | 6.78E+09 | | | | |
| Lithocholic acid (0.5:1) | 6.82E+09 | | | | |
| Lithocholic acid (1:1) | 6.78E+09 | | | | | romethane (8:2) eluent, 5× column volume). The solution was concentrated under reduced pressure, and the resulting solid was crystallized from acetonitrile/dichloromethane (20:1) to afford 2.40 g of DOTAP-Cl and DOTAP-I as a mixture (3:1 by MS).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the relevant fields, are intended to be within the scope of the following claims.

We claim:

1. A composition for transfecting cells comprising:
   (A) an amphipathic compound;
   (B) dioleoylphosphatidylethanolamine (DOPE) wherein the molar ratio of said amphipathic compound to said DOPE is from 10:1 to 1:10; and
   (C) dilauroylphosphatidylcholine (DLPC) wherein the ratio of DOPE to DLPC is approximately 19:1.

2. A process for delivering a nucleic acid to a mammalian cell consisting essentially of:
   (A) forming a composition comprising:
      i) amphipatic compounds capable of complexing nucleic acids;
      ii) cationic polymers;
      iii) a detergent; wherein the molar ratio of the amphipathic compounds to the detergent is 100:1 to 1:100; and,
      iv) the nucleic acid,
   (B) vortexing the composition; and
   (C) contacting the cell with the composition.

3. The process of claim 2, wherein the detergent is dilauroylphosphatidylethanolamine (DLPE).

4. The process of claim 2, wherein the detergent is 3-[(cholamidopropyl)dimethylammonio]-1-propanesulfonate (CHAPS).

5. The process of claim 2 wherein the detergent is selected from the list consisting of: 3-[(cholamidopropyl)dimethylammonio]-1-propanesulfonate (CHAPS), 3-[(cholamidopropyl)dimethylammonio]-2-hydroxy-1-propanesulfonate (CHAPSO), cetyltrimethylammonium bromide (CTAB), dilauroyl phosphatidylethanolamine (DLPE), dilauroylphosphatidylcholine (DLPC) and melittin.

6. The process of claim 2 wherein the amphipathic compound is selected from the list consisting of: 1,4-bis(3-oleoylamidopropyl) piperazine, and 1,2-bis(oleoyloxy)-3-(4'-trimethylammonio)propane (DOTAP).

7. The process of claim 2 wherein the cationic polymer is selected from the list consisting of: histone, polylysine, polyarginine, polyornithine and polyethylenimine.

* * * * *